US008351034B2

(12) United States Patent
Shinoda

(10) Patent No.: US 8,351,034 B2
(45) Date of Patent: Jan. 8, 2013

(54) LAMINAR FLOW WIDTH DETECTING METHOD, LAMINAR FLOW WIDTH CONTROL METHOD, LAMINAR FLOW CONTROL SYSTEM, AND FLOW CYTOMETER

(75) Inventor: Masataka Shinoda, Tokyo (JP)

(73) Assignee: Sony Corporation, Tokyo (JP)

( * ) Notice: Subject to any disclaimer, the term of this patent is extended or adjusted under 35 U.S.C. 154(b) by 455 days.

(21) Appl. No.: 12/328,574

(22) Filed: Dec. 4, 2008

(65) Prior Publication Data
US 2009/0153883 A1      Jun. 18, 2009

(30) Foreign Application Priority Data

Dec. 13, 2007    (JP) ............................... P2007-321543

(51) Int. Cl.
*G01N 15/02* (2006.01)
(52) U.S. Cl. ....................................... 356/335; 356/336
(58) Field of Classification Search ........... 356/335–343
See application file for complete search history.

(56) References Cited

U.S. PATENT DOCUMENTS

| 2002/0141902 A1* | 10/2002 | Ozasa et al. ............... 422/82.09 |
| 2004/0004716 A1* | 1/2004 | Mavliev ......................... 356/336 |
| 2004/0070757 A1* | 4/2004 | Moore et al. .................. 356/339 |

FOREIGN PATENT DOCUMENTS

| JP | 62-100642 | | 5/1987 |
| JP | 63182547 A | * | 7/1988 |
| JP | 363182547 A | * | 7/1988 | ................... 356/335 |
| JP | 1-118747 | | 5/1989 |
| JP | 7-318478 | | 12/1995 |
| JP | 2001-50887 | | 2/2001 |
| JP | 2003-107099 | | 4/2003 |
| JP | 2004-500562 | | 1/2004 |
| JP | 2006-170687 | | 6/2006 |
| JP | 2006-242849 | | 9/2006 |

* cited by examiner

*Primary Examiner* — Tri T Ton
(74) *Attorney, Agent, or Firm* — Finnegan, Henderson, Farabow, Garrett & Dunner LLP

(57) ABSTRACT

The present invention provides a method for detecting the widths of a plurality of laminar layers formed in a channel includes performing at least the steps of: detecting optical information generated from a reference substance contained in a laminar flow; and calculating the width of the laminar flow, based on the optical information detected in the optical information detecting step.

9 Claims, 15 Drawing Sheets

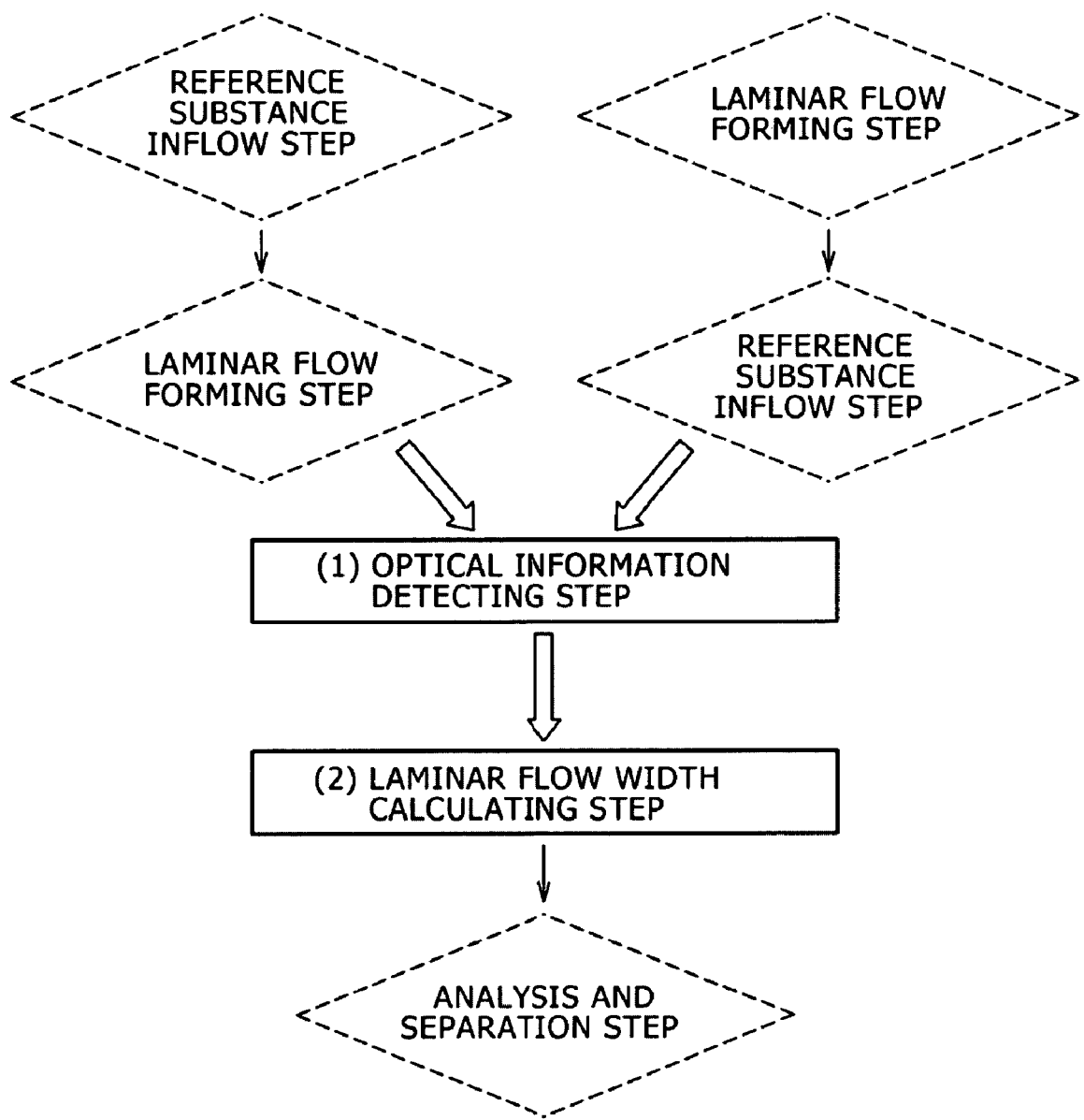
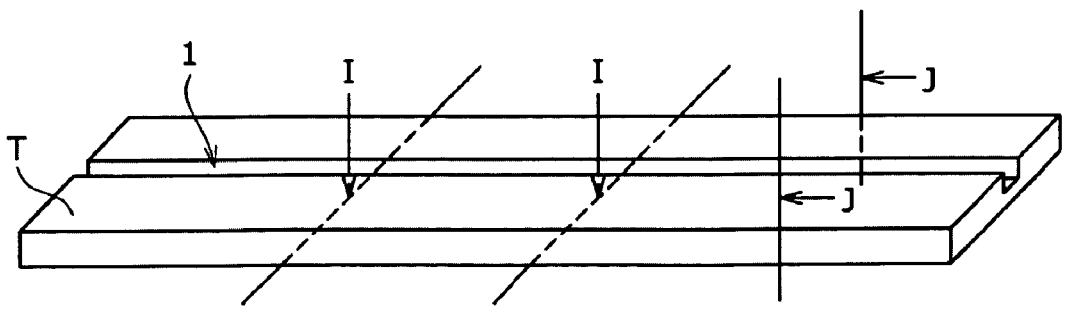

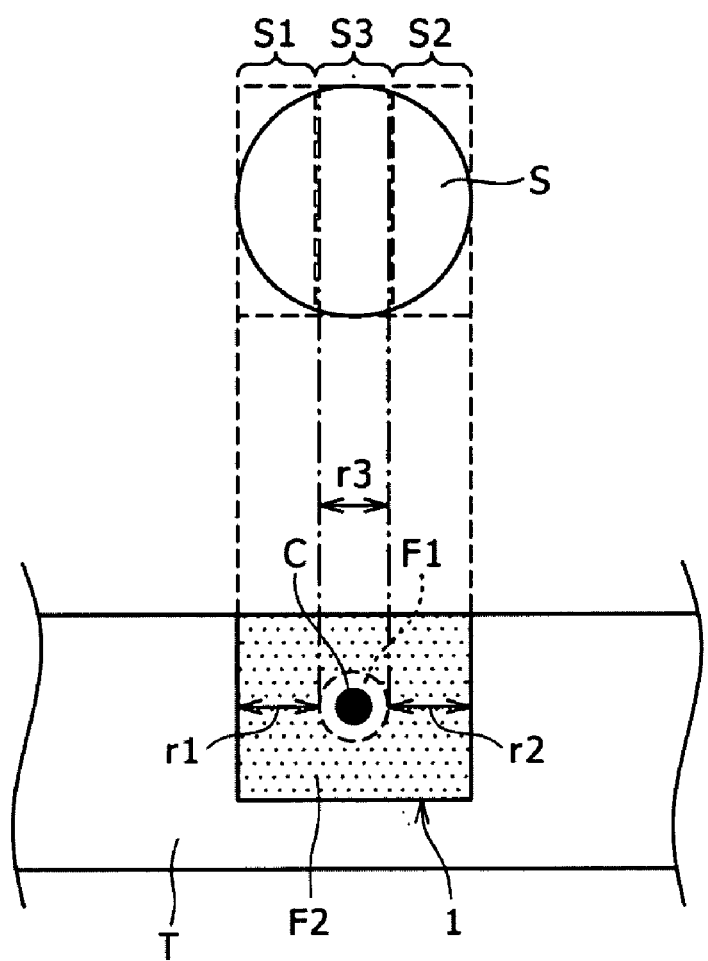

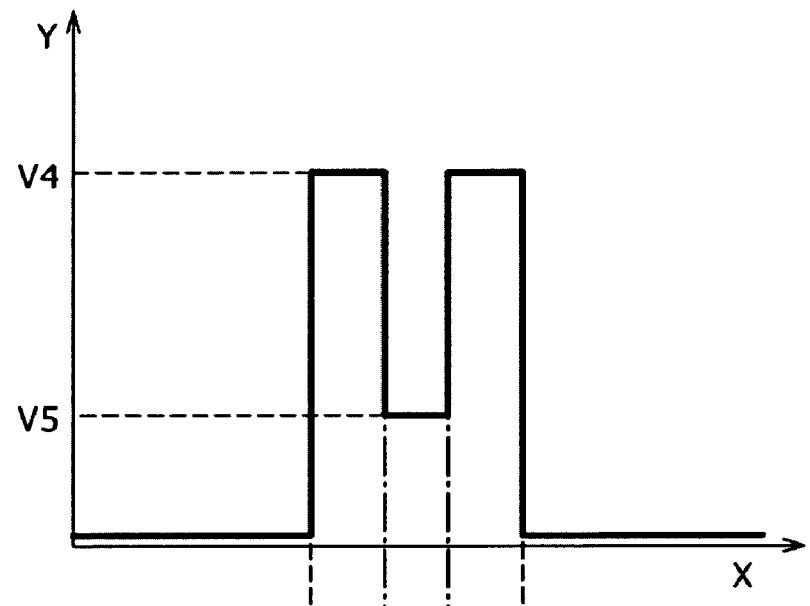
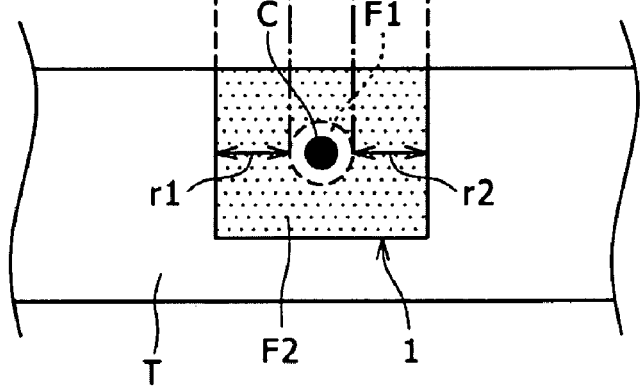

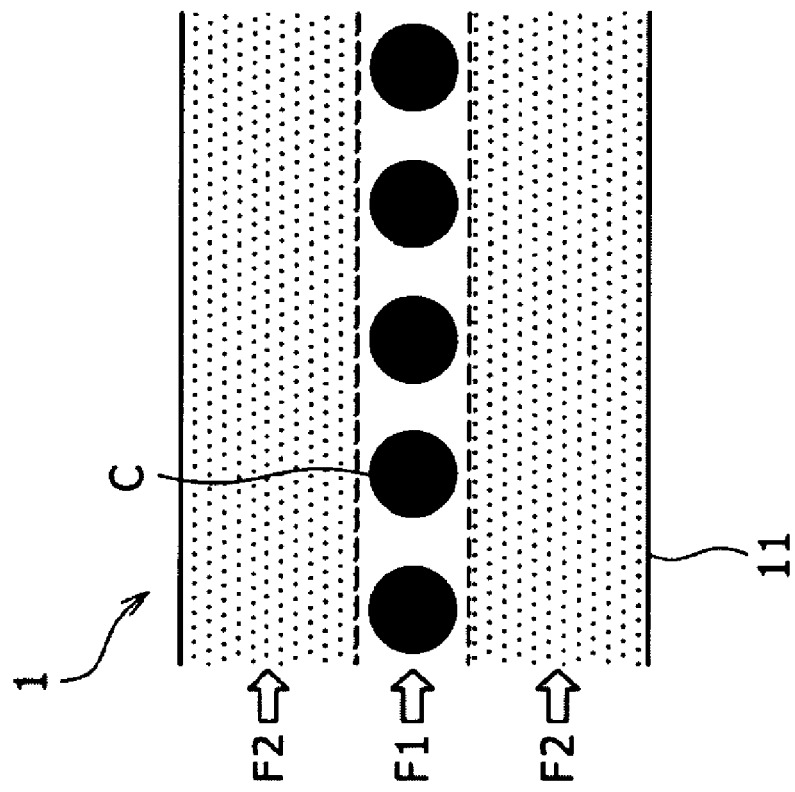
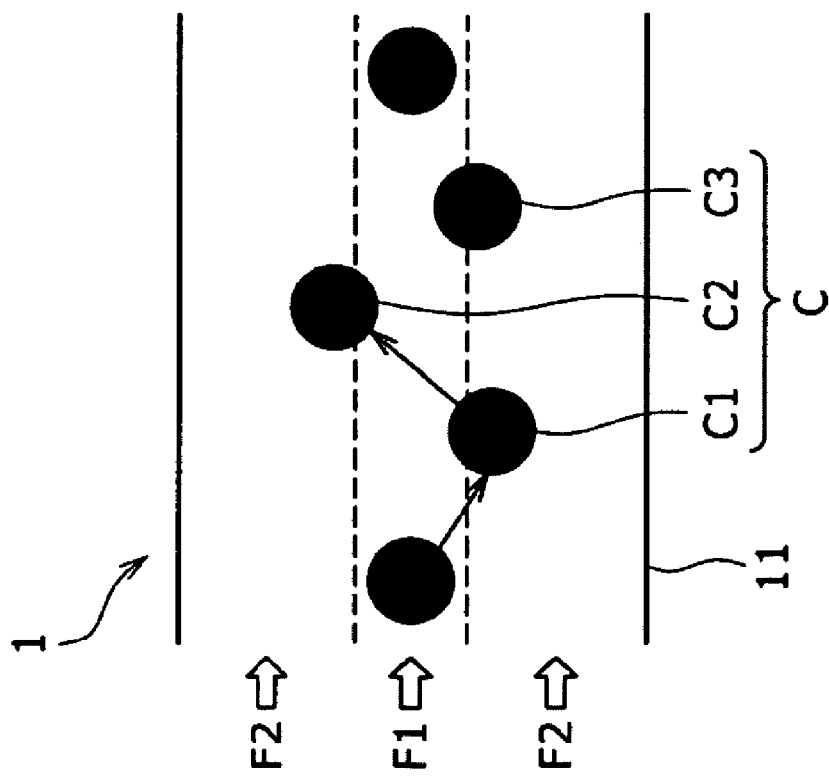

LAMINAR FLOW WIDTH DETECTING METHOD, LAMINAR FLOW WIDTH CONTROL METHOD, LAMINAR FLOW CONTROL SYSTEM, AND FLOW CYTOMETER

CROSS REFERENCES TO RELATED APPLICATIONS

The present invention contains subject matter related to Japanese Patent Application JP 2007-321543, filed in the Japan Patent Office on Dec. 13, 2007, the entire contents of which being incorporated herein by reference.

BACKGROUND OF THE INVENTION

1. Field of the Invention

The present invention relates to a method of detecting the width of a laminar flow. More particularly, the invention relates to a method of detecting the widths of a plurality of laminar flows formed in a channel, a method of controlling the width of a laminar flow, a system for controlling a laminar flow, and a flow cytometer.

2. Description of the Related Art

In recent years, a technology for causing bio-particulates such as cells and microorganisms, particulates such as microbeads, or the like to flow in a two-dimensional or three-dimensional channel formed on a plastic, glass or other substrate, detecting the particulates or the like by a physical means, an optical means or the like, and analyzing and separating the particulates or the like, has been advanced.

The above-mentioned technology has already become one of important basic technologies in diagnosis of diseases, screening of compounds such as drugs, forensic medicine, comprehensive analysis of genetic information, functional analysis of bio-substances, proteome analysis, analysis of in-vivo reactions, food industries, agricultural field, engineering fields, criminal identification field, etc. As one representative example of the method for analyzing or separating particulates or the like by use of a channel as above-mentioned, the analytical method called flow cytometry will be described below.

The flow cytometry is an analytical method in which particulates or the like to be analyzed are caused to flow in a fluid so as to form a row of the particulates, the particulates arrayed in a row are irradiated with a laser beam or the like, and the fluorescence or scattered light generated from each of the particulates is detected so as to analyze the particulates, and, further, the particulates are fractionally collected according to the analytical results.

Now, the flow cytometry will be described in detail below referring to FIG. 18. FIG. 18 is a schematic illustration of the concept of flow cytometry according to the related art. The process of flow cytometry can be largely divided into (i) water flow system, (ii) optical system, (iii) electric system, and (iv) fractional collection system.

(i) Water Flow System

In the water flow system (i), the particulates to be analyzed are arrayed in a row in a flow cell (channel) (see (i) in FIG. 18). More specifically, sheath flows F200 are made to flow at a fixed velocity in the flow cell, and, under this condition, a sample flow F100 containing the particulates is made slowly to flow into a central part of the flow cell. In this instance, by the principle of laminar flow in the channel, the respective flows do not mix with each other, and layer-formed flows (laminar flows) are formed. Then, the inflow quantities of the sheath flows F200 and the sample flow F100 are adjusted according to the size of the particulates to be analyzed or the like so that the particulates are made to flow in the state of being arrayed one after another.

In relation to the water flow system, there has also been developed a technology called micro flow cell or microfluidics in which two-dimensional or three-dimensional fine channels of about 1 mm or below in size formed from a plastic, glass or the like are used.

(ii) Optical System

In the optical system (ii), the particulates to be analyzed are irradiated with a laser beam, and fluorescence or scattered light generated from the particulates is detected (see (ii) in FIG. 18). Specifically, in the water flow system (i), the particulates are made to flow through a laser beam-irradiated part in the state of being arrayed one after another, and the fluorescence or scattered light generated from the particulate each time each of the individual particulates passes is detected by an optical detector on a parameter basis, so as to analyze the characteristics of each of the particulates.

(iii) Electric System

In the electric system (iii), the optical information detected in the optical system (ii) is converted into an electrical signal (voltage pulse) (see (iii) in FIG. 18). The electrical signal converted from the optical information is digitized, and a histogram is extracted based on the digitized data by use of an analyzing computer and software, so as to perform analysis.

(iv) Fractional Collection System

In the fractional collection system (iv), the particulates having undergone the measurement are separated and collected (see (iv) in FIG. 18). Representative fractional collection methods include a method in which a plus or minus electric charge is given to the particulates having undergone the measurement, and two deflection plates D with a potential difference therebetween are disposed on opposite sides of the flow cell so that the electrically charged particulates are each drawn toward either of the deflection plates according to the electric charge given thereto, whereby fractional collection of the particulates is achieved.

As above-mentioned, a technology for analysis and fractional collection of particulates in a channel (flow cell) is demanded in a wide range of fields, and the technology pertaining to the process of (i) to (iv) above has been being developed day by day. For example, JP-t-2004-500562 proposes a technology for stabilizing an astable flow (laminar flow) in which use is made of sheath flows with a thickening agent added thereto in order to provide the sheath flows with a viscosity higher than that of water.

SUMMARY OF THE INVENTION

In the case where a plurality of laminar flows are formed in a channel and particulates or the like are contained in the laminar flow to flow in the channel, if the width of the laminar flow is too large or too small as compared with the particle diameter of the particulates or the like, it is difficult to cause the particulates or the like to flow in the channel in the state of being orderly arrayed in a row. In view of this, it is needed to determine the widths of the plurality of laminar flows formed in the channel or the ratio thereof and to control these factors. According to the related art, however, it has been difficult to detect the widths of the individual laminar flows or the ratio thereof.

Therefore, in order to ensure that the particulates or the like to be analyzed are made to flow in the channel in the state of being orderly arrayed in a row, it may be needed to cause reference spectrum beads, reference diameter beads or the like corresponding to the objective particulates to flow in the channel so as to determine an optimum laminar flow width, prior to causing the objective particulates or the like to flow in the channel. Thus, this technology has involved an intricate work.

In addition, a sample liquid often contains particulates or the like which are different in size or properties. Therefore, there may be cases where it is desired to correct the width of a laminar flow to an optimum value for the objective particulates or the like during the flow of the particulates or the like in the channel. However, the width of a laminar flow set in a step prior to the actual flowing of the objective particulates or the like is difficult to detect during the flowing of the particulates. Thus, it has been difficult to control the width of the laminar flow.

Furthermore, in the channel, the width of the laminar flow set in the step prior to the actual flowing of the objective particulates or the like may vary under the influences of the surface tension on the channel wall or the like factors. However, like the above-mentioned cases, the width of the laminar flow set in a step prior to the actual flowing of the objective particulates or the like is difficult to detect during the flowing of the particulates in the channel. Thus, it has been difficult to control the width of the laminar flow.

Accordingly, there is a need to provide a novel laminar flow width detecting method by which the widths of a plurality of laminar flows formed in a channel can be detected easily.

According to one embodiment of the present invention, there is provided a laminar flow width detecting method for detecting the widths of a plurality of laminar flows formed in a channel, the method including performing at least the steps of:

detecting optical information generated from a reference substance contained in a laminar flow; and calculating the width of the laminar flow, based on the optical information detected in the optical information detecting step.

The laminar flow width detecting method can also be used in a flow cytometer. For example, in a flow cytometer, the reference substance may be contained in a sheath flow surrounding a sample flow formed in a channel, whereby the widths of the sample flow and the sheath flow can be detected.

The reference substance which can be used in the laminar flow width detecting method according to the one embodiment of the present invention is not particularly limited. For example, a fluorescent substance can be used as the reference substance.

According to another embodiment of the present invention, there is provided a laminar flow width control method for controlling the widths of a plurality of laminar flows formed in a channel, the method including performing at least the steps of:

detecting optical information generated from a reference substance contained in a laminar flow;

calculating the width of the laminar flow, based on the optical information detected in the optical information detecting step; and adjusting the liquid feed quantity of the laminar flow, based on the width of the laminar flow calculated in the laminar flow width calculating step.

The laminar flow width control method can also be used in a flow cytometer. For example, in a flow cytometer, the reference substance is contained in a sheath flow surrounding a sample flow formed in a channel, whereby the widths of the sample flow and the sheath flow can be controlled.

In the liquid feed quantity adjusting step, the liquid feed quantities can be controlled according to various purposes.

For example, the liquid feed quantities of the sample flow and the sheath flow can be controlled according to the particle diameter of the sample.

The reference substance which can be used in the laminar flow width control method according to the another embodiment of the present invention is not particularly limited. For example, a fluorescent substance can be used as the reference substance.

According to a further embodiment of the present invention, there is provided a laminar flow control system for controlling the widths of a plurality of laminar flows formed in a channel, the system including at least:

a section for detecting optical information generated from a reference substance contained in a laminar flow;

a section for calculating the width of the laminar flow, based on the optical information detected by the optical information detecting section; and a section for adjusting the liquid feed quantity of the laminar flow, based on the width of the laminar flow calculated by the laminar flow width calculating section.

According to yet another embodiment of the present invention, there is provided a flow cytometer capable of controlling the widths of a sample flow and a sheath flow surrounding the sample flow which are formed in a channel, the cytometer including at least:

a section for detecting optical information generated from a reference substance contained in the sheath flow;

a section for calculating the widths of the sample flow and the sheath flow, based on the optical information detected by the optical information detecting section; and a section for adjusting the liquid feed quantities of the sample flow and the sheath flow, based on the widths of the sample flow and the sheath flow calculated by the laminar flow width calculating section.

In the liquid feed quantity adjusting section, the liquid feed quantities are adjusted according to various purposes. For instance, the liquid feed quantities of the sample flow and the sheath flow can be adjusted according to the particle diameter of the sample.

In the laminar flow width detecting method according to one embodiment of the present invention, the reference substance is contained in a laminar flow, so that the specific widths of the plurality of laminar flows formed in the channel can be detected easily. Therefore, the control of the widths of the laminar flows can also be performed easily. Accordingly, it is possible to enhance the accuracy in analysis, separation or the like of the objective particulates or the like, and to promise large reductions in time and cost.

BRIEF DESCRIPTION OF THE DRAWINGS

FIG. 1 is a flow chart of a laminar flow width detecting method according to one embodiment of the present invention;

FIG. 2 is a perspective schematic view of a channel formed on a substrate;

FIGS. 5A and 5B illustrate a laminar flow width calculating step in the case of using a bisection-type photo-detector, wherein FIG. 5A is a schematic view from above of a light irradiation spot in irradiating a predetermined portion of the channel with light in the optical information detecting step, and FIG. 5B is a sectional schematic view of the channel taken along line J-J, i.e., as viewed in the direction of arrows J, of FIG. 2;

FIGS. 6A and 6B illustrate a laminar flow width calculating step in the case of using a bisection-type photo-detector, wherein FIG. 6A is a schematic view from above of a light irradiation spot in irradiating a predetermined portion of the channel with light in the optical information detecting step, and FIG. 6B is a sectional schematic view of the channel taken along line J-J, i.e., as viewed in the direction of arrows J, of FIG. 2;

FIGS. 7A and 7B illustrate a laminar flow width calculating step in the case of using a trisection-type photo-detector, wherein FIG. 7A is a schematic view from above of a light irradiation spot in irradiating a predetermined portion of the channel with light in the optical information detecting step, and FIG. 7B is a sectional schematic view of the channel taken along line J-J, i.e., as viewed in the direction of arrows J, of FIG. 2;

FIGS. 8A and 8B illustrate a laminar flow width calculating step in the case of using a trisection-type photo-detector, wherein FIG. 8A is a schematic view from above of a light irradiation spot in irradiating a predetermined portion of the channel with light in the optical information detecting step, and FIG. 8B is a sectional schematic view of the channel taken along line J-J, i.e., as viewed in the direction of arrows J, of FIG. 2;

FIG. 9A is a graph substituting for a view for indicating the amount of detection signal of optical information, and FIG. 9B is a sectional schematic view of a channel taken along line J-J, i.e., as viewed in the direction of arrows J, of FIG. 2;

FIG. 10A is an illustration of a related-art method for forming a laminar layer containing objective particulates in a central part of a channel, and FIG. 10B is a sectional schematic illustration of the method of forming a laminar flow containing objective particulates in a central part of a channel in the laminar flow width detecting method according to one embodiment of the present invention;

DETAILED DESCRIPTION OF THE PREFERRED EMBODIMENT

Figure 3:
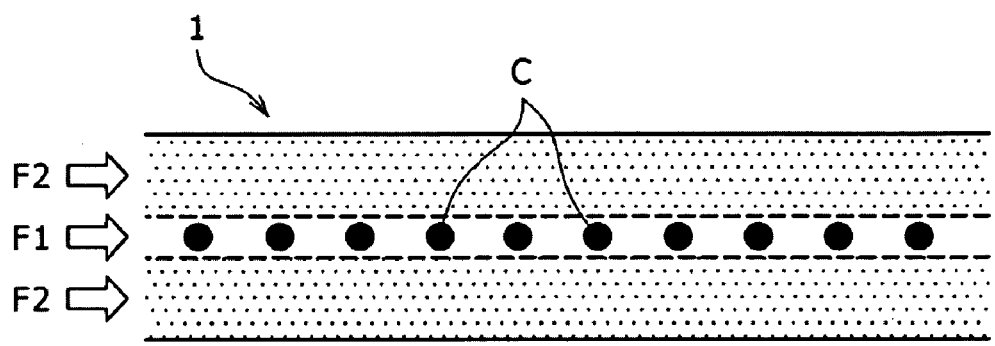
FIG. 3 is a sectional schematic view of the channel taken along line I-I, i.e., as viewed in the direction of arrows I, of FIG. 2.

Now, a preferred embodiment of carrying out the present invention will be described below, referring to the drawings. Incidentally, the embodiment described below is merely an example of representative embodiment of the present invention, and is not to be construed as limitative of the invention.

<Laminar Flow Width Detecting Method>

FIG. 1 is a flow chart of a laminar flow width detecting method according to one embodiment of the present invention.

The laminar flow width detecting method according to one embodiment of the present invention is a method for detecting the widths of a plurality of laminar flows formed in a channel, and includes performing at least an optical information detecting step (1) and a laminar flow width calculating step (2). Now, the individual steps will be described in detail below.

Figure 4:
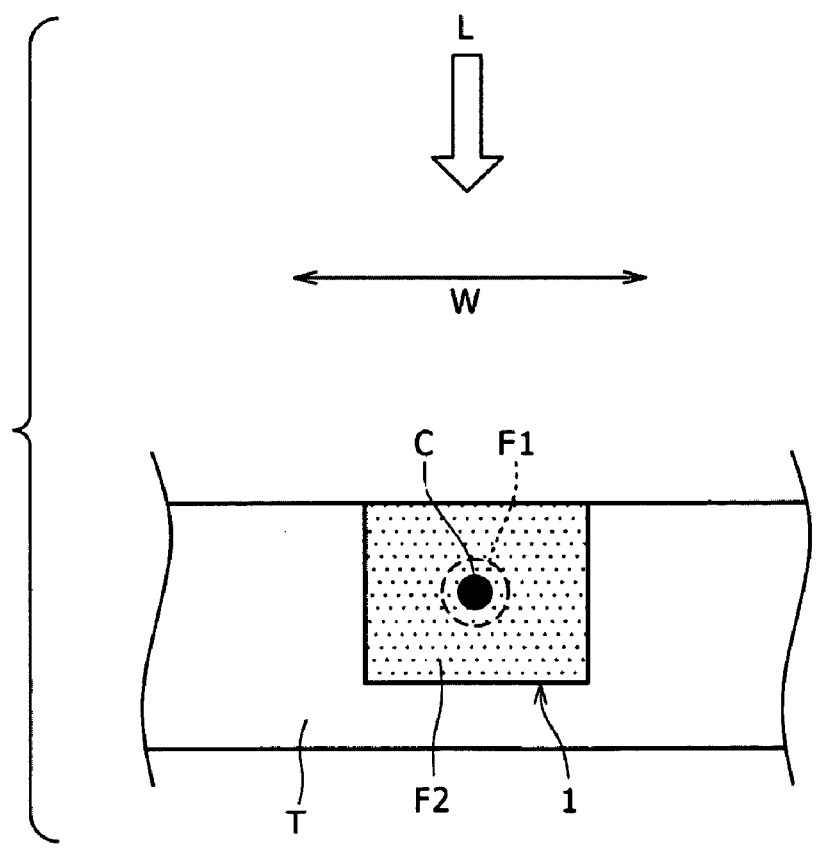
FIG. 4 is a sectional schematic view of the channel taken along line J-J, i.e., as viewed in the direction of arrows J, of FIG. 2.

FIG. 2 is a perspective schematic view of a channel 1 formed on a substrate T; FIG. 3 is a sectional perspective view of the channel 1 taken along line I-I, namely, as viewed in the direction of arrows I, of FIG. 2; and FIG. 4 is a sectional schematic view of the channel 1 taken along line J-J, namely, as viewed in the direction of arrow J, of FIG. 2. Incidentally, a substrate for confining the channel 1 is not shown in the drawings.

The form of the channel 1 with which the laminar flow width detecting method according to one embodiment of the present invention can be carried out is not particularly limited, and can be designed freely, insofar as laminar flows can be formed therein. For example, as shown in FIG. 2, a two-dimensional or three-dimensional channel 1 formed on a substrate T formed from a plastic, glass or the like can be used to carry out the laminar flow width detecting method according to one embodiment of the present invention.

In addition, the width of the channel 1 is not particularly limited, and can be designed freely, insofar as laminar flows can be formed in the channel 1. For example, a micro flow cell with a channel width of 1 mm or below can be used to carry out the laminar flow width detecting method according to one embodiment of the present invention. Particularly, when a micro flow cell with a channel width of about 10 μm to about 1 mm is used, the laminar flow width detecting method according to one embodiment of the present invention can be carried out suitably.

In the channel 1, a plurality of laminar flows are formed. The number of the laminar flows is not particularly limited, and can be adjusted according to the purpose. For example, in FIG. 3, three laminar flows as viewed in section are formed so that a laminar flow of a sample flow F1 containing particulates C to be analyzed and separated is sandwiched between fluid media (hereinafter referred to as "sheath flows F2") denoted by symbol F2 in FIG. 3. However, two laminar flows may be formed, or four or more laminar flows may be formed, in carrying out the laminar flow width detecting method according to one embodiment of the present invention.

Besides, a reference substance is contained in at least one laminar flow selected from among the sample flow F1 and the sheath flows F2. The laminar flow(s) in which to contain the reference substance is not particularly limited, and can be appropriately adjusted according to the laminar flow whose width is desired to be detected. For example, in FIG. 3, the reference substance is contained in the sheath flows F2.

The method for containing the reference substance in at least one of the sample flow F1 and the sheath flows F2 is not particularly limited, and can be selected from among various methods (refer to the flow chart in FIG. 1). For example, a method may be used in which a plurality of laminar flows (sample flow F1, sheath flow F2) are formed in the channel 1, and thereafter the reference substance is put into the objective laminar flow(s). Also, a method may be used in which a plurality of laminar flows (sample flow F1, sheath flow F2) are formed in the channel 1 by use of a fluid medium or the like in which the reference substance is preliminarily contained.

The reference substance is not particularly limited, insofar as it permits detection of optical information in an optical information detecting step (1) which will be described later. Examples of the reference substance which can be used include fluorescent substances such as fluorescent coloring matters, etc., and microbeads, etc., among which the fluorescent coloring matters are more preferred in view of the size thereof. The kind of the fluorescent coloring matter to be used can be selected freely. Examples of the fluorescent coloring matter to be used include Cascade Blue, Fluorescein isothiocyanate (FITC), Phycoerythrin (PE), Phycoerythrin-Cy5 (PE-Cy5), Phycoerythrin-Cy7 (PE-Cy7), Texas Red, Allophycocyanin (APC), and Allophycocyanin-Cy7 (APC-Cy7).

(1) Optical Information Detecting Step

The optical information detecting step (1) is a step of detecting optical information from the reference substance contained in a laminar flow (here, the sheath flows F2), at a predetermined position of the channel 1. Specifically, the laminar flows (here, the sheath flows F2) containing the reference substance are formed in the channel 1, a predetermined portion of the channel 1 is irradiated with light in the direction of arrow L in FIG. 4, for example, and fluorescence or scattered light generated from the reference substance upon the irradiation with light is detected by a photo-detector.

The kind of light irradiation in the optical information detecting step (1) is not particularly limited. However, light which is constant in direction, wavelength and intensity is used desirably, in order for the fluorescence or scattered light to be securely generated from the reference substance and the particulates C. Examples of the light which can be used favorably include laser light and light from an LED (Light Emission Diode).

In the optical information detecting step (1), the light irradiation method is not particularly limited, insofar as the method permits detection of optical information from the reference substance and the particulates C. For instance, the optical information may be detected while scanning an irradiation spot in the channel width direction as indicated by symbol W in FIG. 4.

The photo-detector to be used in the optical information detecting step (1) is not particularly limited, and known photo-detectors can be used, insofar as the it is possible by the photo-detector to detect optical information from the reference substance. As for the kind of the photo-detector, the bisection type and the trisection type and the like can be used.

(2) Laminar Flow Width Calculating Step

The laminar flow width calculating step (2) is a step of calculating the widths of the laminar flows (sample flow F1, sheath flow F2), based on the optical information detected in the optical information detecting step. This step will now be specifically described, referring to FIGS. 5A to 9B.

Figure 5A:
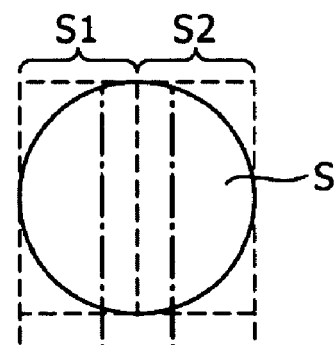
Figure 5B:
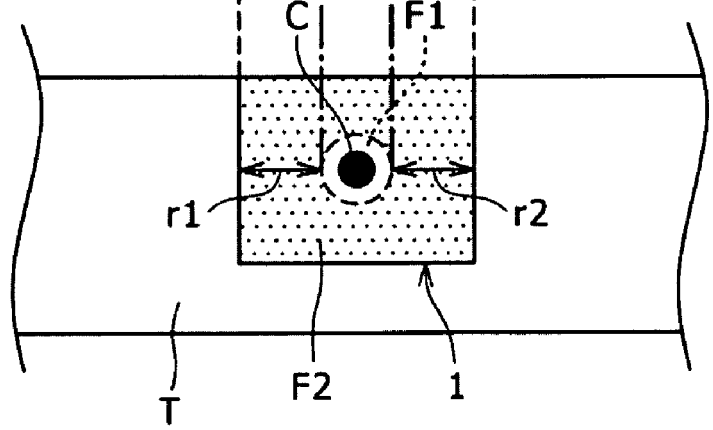

FIGS. 5A and 5B illustrate the laminar flow width calculating step in the case of using a bisection-type photo-detector. FIG. 5A is a schematic view from above of a light irradiation spot S in irradiating a predetermined portion of the channel 1 with light in the optical information detecting step (1), and FIG. 5B is a sectional schematic view of the channel 1 taken along line J-J, namely, as viewed in the direction of arrows J, of FIG. 2.

In the case where the intensity V1 of optical information detected from a light irradiation spot S1 in FIG. 5A and the intensity V2 of optical information detected from a light irradiation spot S2 are equal, it can be confirmed by calculation that the laminar flow widths denoted by symbols r1 and r2 in FIG. 5B are equal.

Figures 6A, 6B:
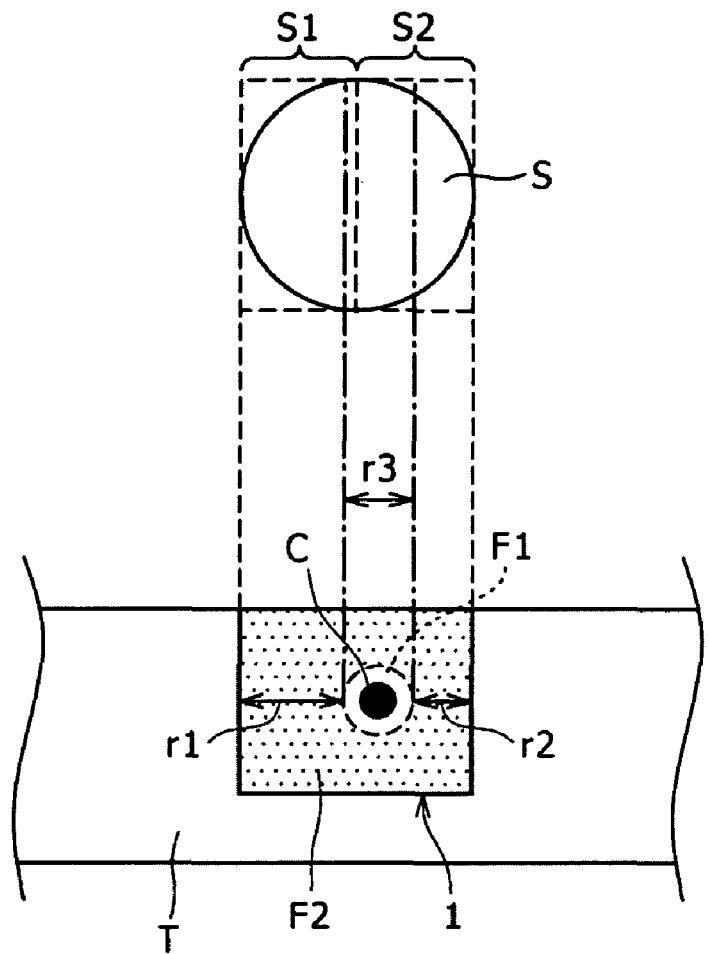

Alternatively, in the case where the intensity V1 of optical information detected from a light irradiation spot S1 and the intensity V2 of optical information detected from a light irradiation spot S2 are in the relation of V1>V2, as shown in FIGS. 6A and 6B, it can be confirmed by calculation that the laminar flow widths of the sheath flows F2 are in the relation of r1>r2.

Besides, when the relationships between the intensities V1, V2 of optical information and the laminar flow widths r1, r2 are preliminarily determined, the laminar flow width r1 and the laminar flow width r2 can be calculated by determining the intensity V1 of optical information detected from the light irradiation spot S1 and the intensity V2 of optical information detected from the light irradiation spot S2.

Furthermore, once the laminar flow width r1 and the laminar flow width r2 can be calculated, the laminar flow width r3 of the sample flow F1 can also be calculated by subtracting the laminar flow widths r1 and r2 from the width of the channel 1.

FIGS. 7A and 7B illustrate the laminar flow width calculating step in the case of using a trisection-type photo-detector. FIG. 7A is a schematic view from above of a light irradiation spot in the case of irradiating a predetermined portion of the channel 1 with light in the optical information detecting step (1), and FIG. 7B is a sectional schematic view of the channel 1 taken along line J-J, namely, as viewed in the direction of arrows J, of FIG. 2.

In the case as illustrated in FIGS. 7A and 7B, the intensity V1 of optical information detected from a light irradiation spot S1 and the intensity V2 of optical information detected from a light irradiation spot S2 are considered to be equal. In this case, the laminar flow widths denoted by symbols r1 and r2 in FIG. 7B of the sheath flows F2 can be calculated to be equal, at the spots S1 and S2.

Besides, when the relationship between the intensity V3 of optical information detected from a light irradiation spot S3 and the laminar flow width r3 are preliminarily determined, the laminar flow width r3 of the sample flow can be calculated by determining the intensity V3 of optical information detected from the light irradiation spot S3.

Figures 8A, 8B:
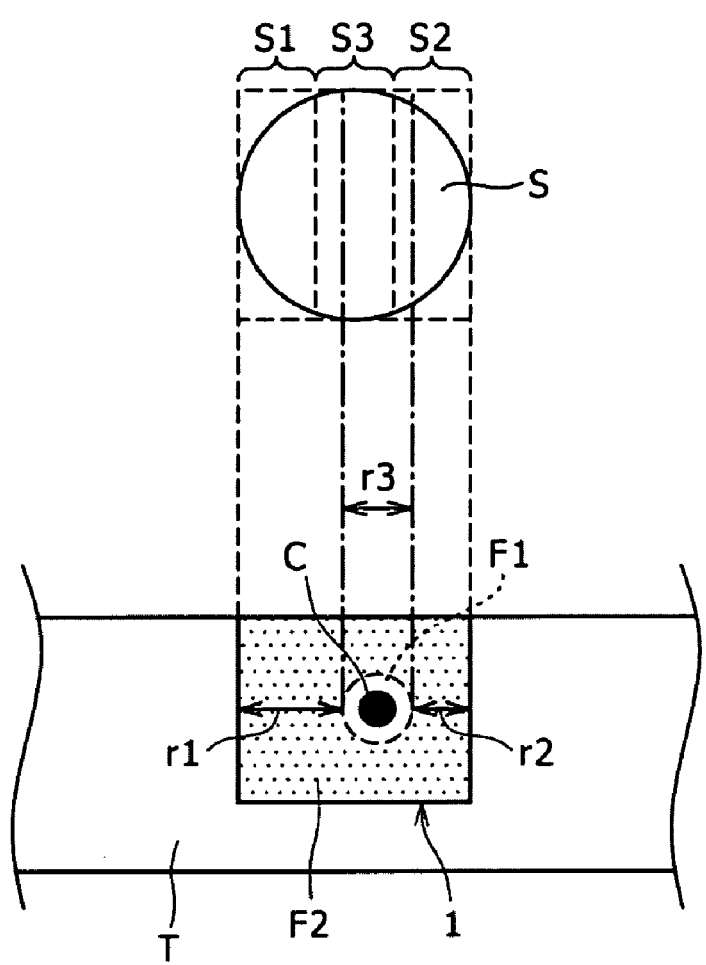

Alternatively, in the case as illustrated in FIGS. 8A and 8B, the intensity V1 of optical information detected from a light irradiation spot S1 and the intensity V2 of optical information detected from a light irradiation spot S2 are considered to be in the relation of V1>V2. In this case, it is confirmed by calculation that the laminar flow widths of the sheath flows F2 are in the relation of r1>r2.

In addition, when the relationships between the intensities V1, V2, V3 of optical information and the laminar flow widths r1, r2, r3 are preliminarily determined, the laminar flow width r1 and the laminar flow width r2 of the sheath flows F2 and the laminar flow width r3 of the sample flow F1 can be calculated by determining the intensities V1, V2, V3 of optical information detected from the light irradiation spot S S1, S2, S3.

Furthermore, in the laminar flow width detecting method according to one embodiment of the present invention, optical information can be detected while scanning the light irradiation spot S in the width direction of the channel 1 (refer to symbol W in FIG. 4). In this case, for example, detection results as shown in FIG. 9A can be obtained. In FIG. 9A, the X-axis represents the light irradiation (scanning) direction, and the Y-axis represents the amount of detection signal.

Since the sheath flows F2 contain the reference substance, a large detection signal amount (refer to symbol V4 in FIG.

9A) is shown in the case where only the sheath flow F2 is present at the light irradiation position in the channel 1. On the other hand, in the case where the sample flow F1 is present, the quantity of the sheath flow F2 is reduced, and the amount of detection signal from the reference substance contained in the sheath flow F2 is also reduced (refer to symbol V5 in FIG. 9A).

Therefore, if the detection signal amount as shown in FIG. 9A can be determined by detecting the optical information while scanning the light irradiation spot S in the width direction of the channel 1, it is possible to easily calculate the laminar flow width r1 and the laminar flow width r2 of the sheath flows F2 in the channel 1 and the laminar flow width r3 of the sample flow F1.

In the method according to the related art, there has been no means for calculating the widths of the laminar flows (sample flow F1, sheath flows F2) in the channel 1. Therefore, in the case where information on the particulates C cannot be detected during analysis or separation, it has been difficult to determine whether the particulates C are absent or the particulates C are not being irradiated securely with light in the irradiation spot.

On the contrary, when the laminar flow width detecting method according to one embodiment of the present invention is used, the widths of the laminar flows (sample flow F1, sheath flows F2) in the channel 1 can be calculated. Therefore, the light receiving position, the size of the light irradiation spot S or the like can be so set that the particulates C are irradiated securely with light in the light irradiation spot, and the accuracy in analysis and/or separation of the particulates C can be enhanced.

In addition, since the reference substance is contained in the sheath flows F2 other than the sample flow F1 containing the particulates C, the following effects are also formed.

In the related art, in the case of analysis or separation or the like of particulates C flowing through a channel 1, a method has been used in which a laminar flow containing the objective particulates C (sample flow F1) is formed in a central part of the channel 1, and radiation of light toward the particulates C or the like operation is conducted so as to perform analysis, separation or the like of the particulates C. In such a method, however, only the information from the particulates C can be obtained during the analysis or separation. Therefore, optimal optical conditions and electrical conditions or the like for the analysis or separation or the like are difficult to obtain through control during measurement. Accordingly, determination of optimal optical conditions and electrical conditions or the like for analysis or separation or the like by causing reference spectrum beads or reference diameter beads or the like corresponding to the particulates C to flow in the channel has to be carried out, prior to the actual measurement; thus, a preparatory step is needed.

On the other hand, in the laminar flow width detecting method according to one embodiment of the present invention, a reference substance is contained in the sheath flows F2 other than the sample flow F1 containing the particulates C, so that information from the reference substance other than the particulates C can also be simultaneously detected during the analysis or separation. Therefore, the control for obtaining the optimal optical conditions and electrical conditions or the like for analysis or separation or the like can be easily carried out even during the analysis or separation. Specifically, the optical conditions include the shape of the irradiation spot, light irradiation intensity, pulse width, the duty ratio of pulses, focal position, etc., whereas the electrical conditions include the amplification factor of the photo-detector, the amplification factor of the light irradiation unit, etc. This promises a shortening of the measurement time and realizes enhancement of the accuracy in analysis, separation or the like.

Besides, in the related art, in the case of forming the laminar flow containing the objective particulates C (sample flow F1) in a central part of a channel 1, the laminar flows are so formed as to sandwich the sample flow F1 between fluid media not containing any reference substance or the like. In this case, in the channel, there is an influence of the surface tension on the wall surfaces 11 of the channel 1, so that it is difficult for the particulates C to flow in the state of being orderly arrayed in a row. For example, there have been cases where the particulates C are attracted toward the side of the wall surface 11 of the channel 1 due to the surface tension on the wall surface, as indicated by symbols C1, C2, C3 in FIG. 10A, possibly leading to a change in the sequence of the particulates C.

However, where the reference substance is contained in the sheath flows F2 as in the laminar flow width detecting method according to one embodiment of the present invention, the influence of the surface tension on the wall surface 11 of the channel 1 can be reduced, and it is possible to cause the particulates C to flow in the state of being orderly arrayed in a row, as shown in FIG. 10B.

<Laminar Flow Width Control Method>

Figure 11:
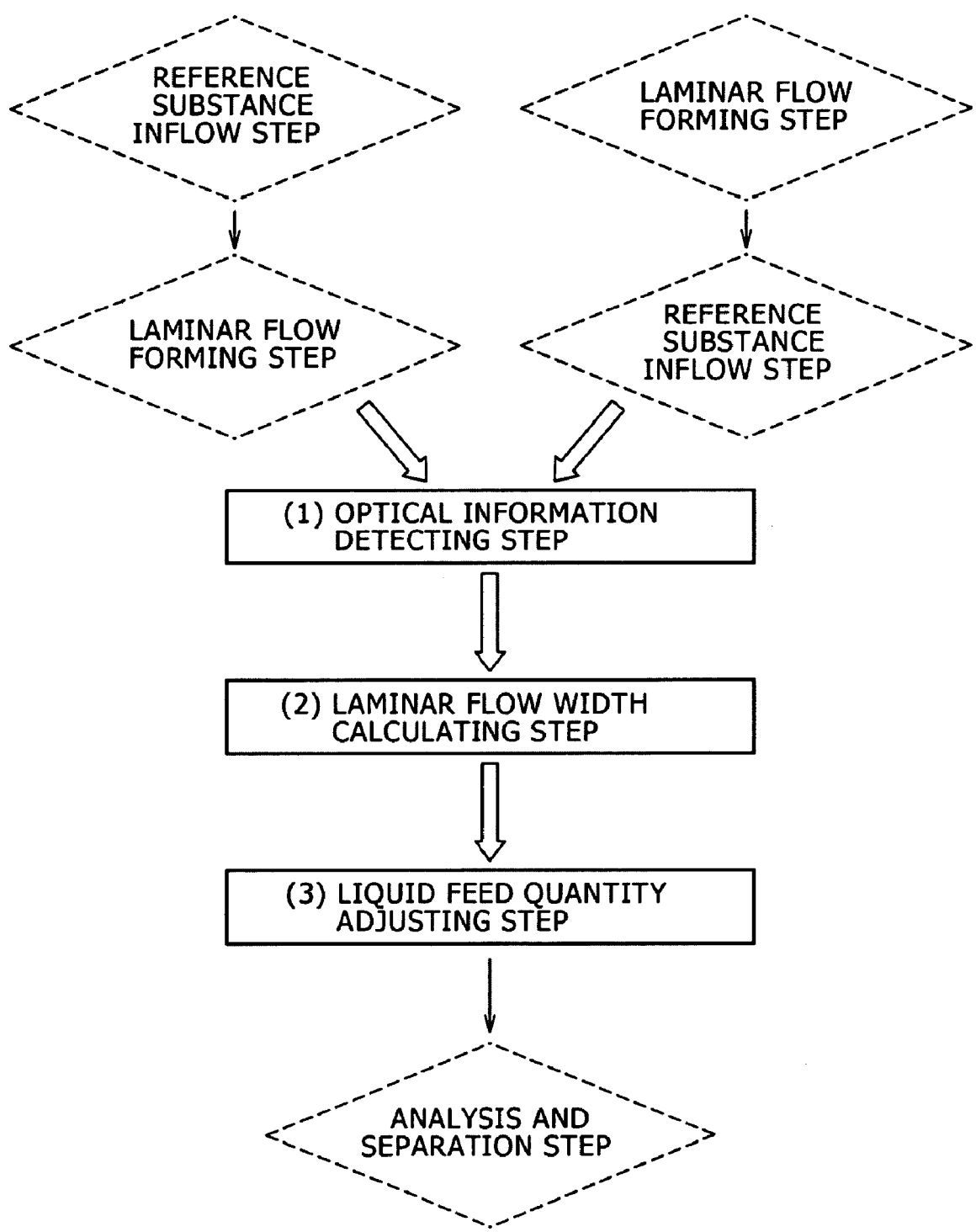
FIG. 11 is a flow chart of a laminar flow width control method according to one embodiment of the present invention.

FIG. 11 is a flow chart of the laminar flow width control method according to one embodiment of the present invention. The laminar flow width control method according to one embodiment of the present invention is a method for controlling the widths of a plurality of laminar flows formed in a channel, which includes performing at least (1) optical information detecting step, (2) a laminar flow width calculating step, and (3) a liquid feed quantity adjusting step. The individual steps will now be described in detail below. Incidentally, the optical information detecting step (1) and the laminar flow width calculating step (2) are the same as the optical information detecting step (1) and the laminar flow width calculating step (2) in the laminar flow width detecting method described above, and, therefore, detailed description of these steps (1) and (2) are omitted here.

(3) Liquid Feed Quantity Adjusting Step

The liquid feed quantity adjusting step (3) is a step of adjusting the liquid feed quantity (quantities) of the laminar flow(s), based on the laminar flow widths calculated in the laminar flow width calculating step (2). A specific method of carrying out this step (3) will now be described referring to FIGS. 12 to 14.

Figure 12:
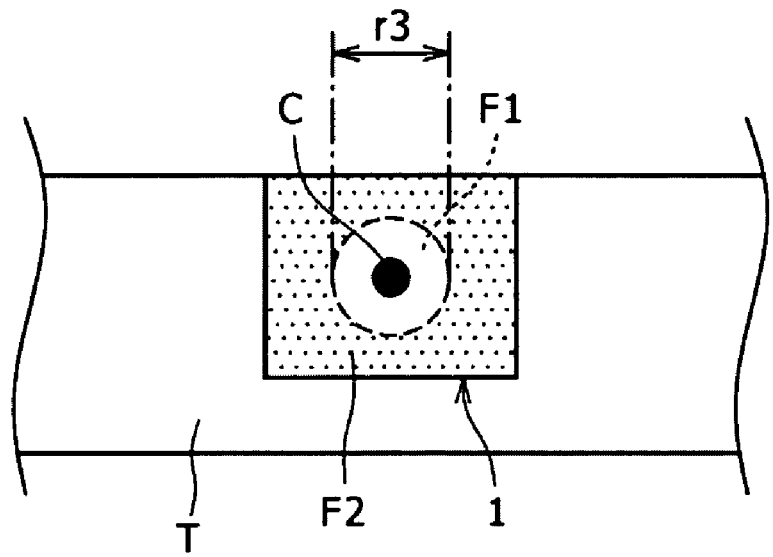
FIG. 12 is a sectional schematic view of a channel taken along line J-J, i.e., as viewed in the direction of arrow J, of FIG. 2.
Figure 13:
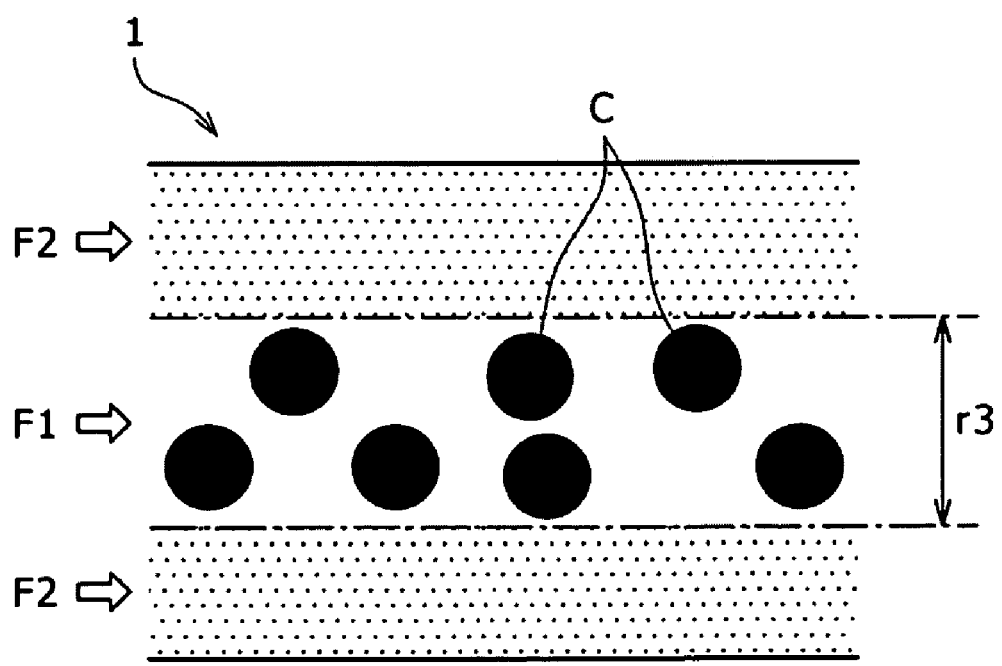
FIG. 13 is a sectional schematic view of the channel taken along line I-I, i.e., as viewed in the direction of arrows I, of FIG. 2.

FIG. 12 is a sectional schematic view of the channel 1 taken along line J-J, namely, as viewed in the direction of arrows J, of FIG. 2. In the case where the laminar flow width r3 of the sample flow L1 calculated in the laminar flow width calculating step (2) is found to be larger than the particle diameter of the particulates C to be analyzed and separated, as shown in FIG. 12, for example, two or more particulates C may overlap with each other in the width direction of the channel 1 in their flowing in the channel 1, as shown in FIG. 13, possibly leading to a change in the sequence of the particulates C. Thus, it is difficult for the particulates C to flow in the state of being orderly arrayed in a row in the channel 1.

In view of this, the liquid feed quantities of the sheath flows F2 are increased to thereby enlarge the laminar flow widths of the sheath flows F2, whereby the laminar flow widths can be so controlled that the laminar flow width r3 of the sample flow F1 is reduced.

Figure 14:
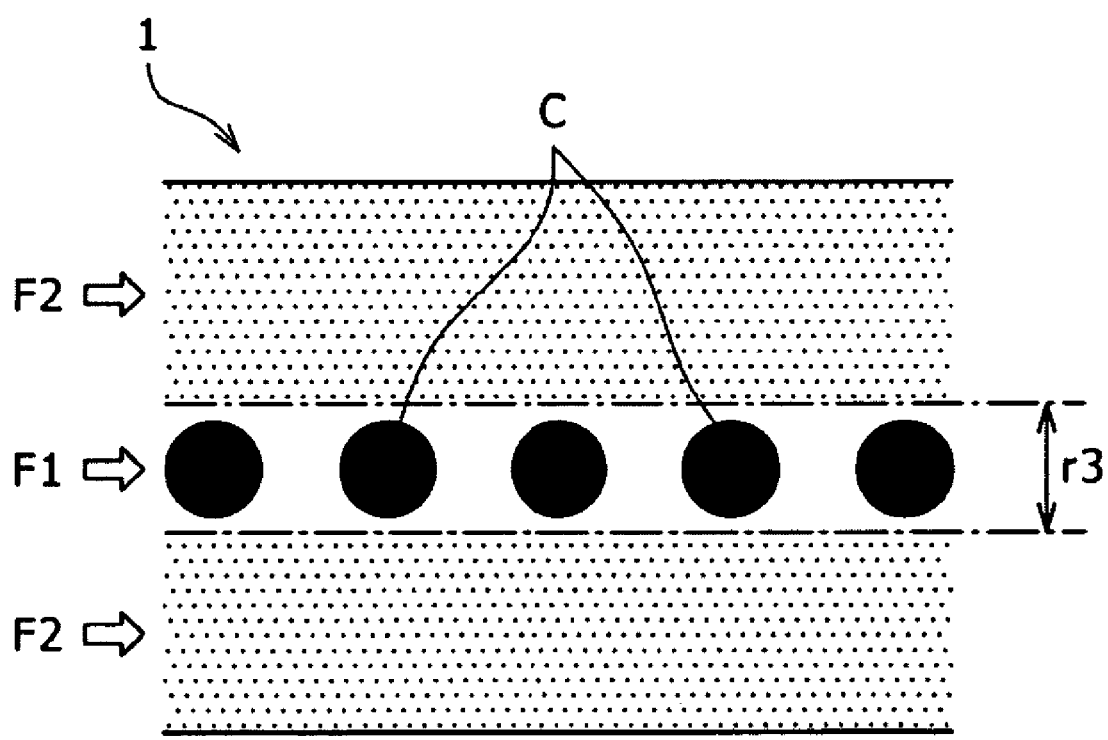
FIG. 14 is a sectional schematic view of the channel taken along line I-I, i.e., as viewed in the direction of arrows I, of FIG. 2.

When the laminar flow width r3 of the sample flow F1 is thus controlled according to the particle diameter of the sample such as the particulates C, the particulates C can be made to flow in the state of being orderly arrayed in a row, as shown in FIG. 14.

Besides, other than the control of the laminar flow width r3 of the sample flow F1 according to the particle diameter of the sample such as the particulates C, it is also possible, for example, to control the laminar flow width r3 of the sample flow F1 according to the light receiving position or size of the light irradiation spot S or the like factor.

Furthermore, though not shown in the drawings, for example in the case where deviation of the sample flow F1 from the central part of the channel 1 is detected, not only the laminar flow width r3 of the sample flow F1 but also the positions of the laminar flows can also be controlled by adjusting the liquid feed quantities of the sheath flows F2, similarly to the above.

Figure 15:
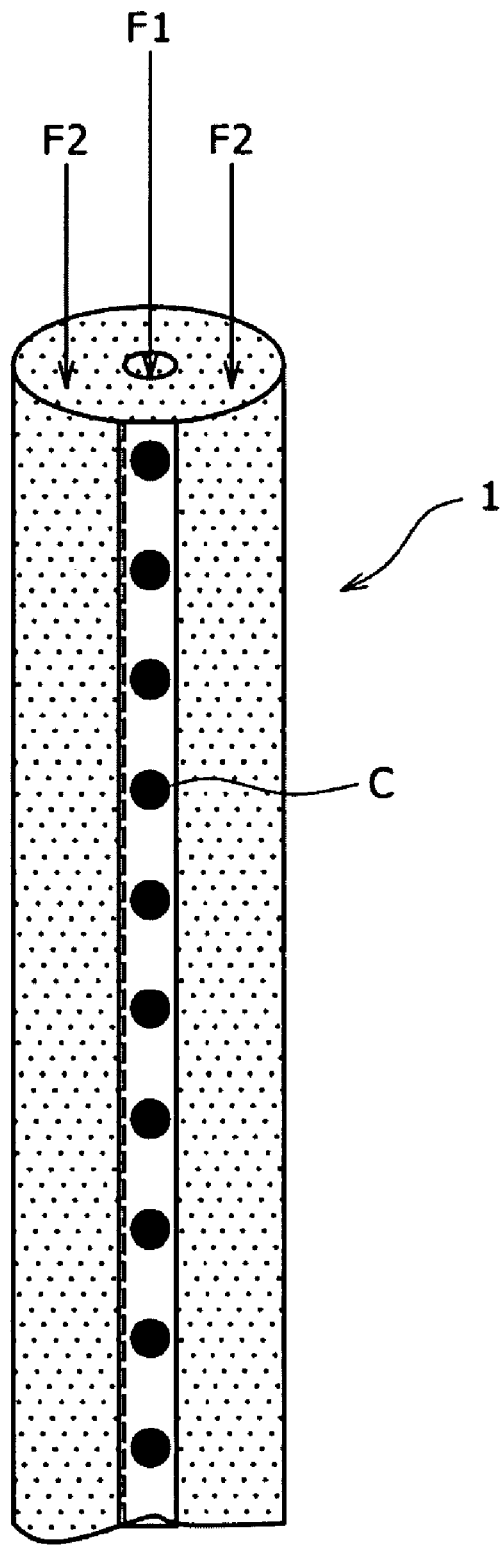
FIG. 15 is a perspective schematic illustration of an example of a channel which can be used in the laminar flow width detecting method and the laminar flow width control method according to embodiments of the present invention.

The laminar flow width detecting method and the laminar flow width control method as above-described are applicable not only to the channel 1 formed on the substrate T but also to any of such known channels 1 as shown in FIG. 15. Especially, the methods are suitably applicable also to flow cytometers.

<Laminar Flow Control System>

Figure 16:
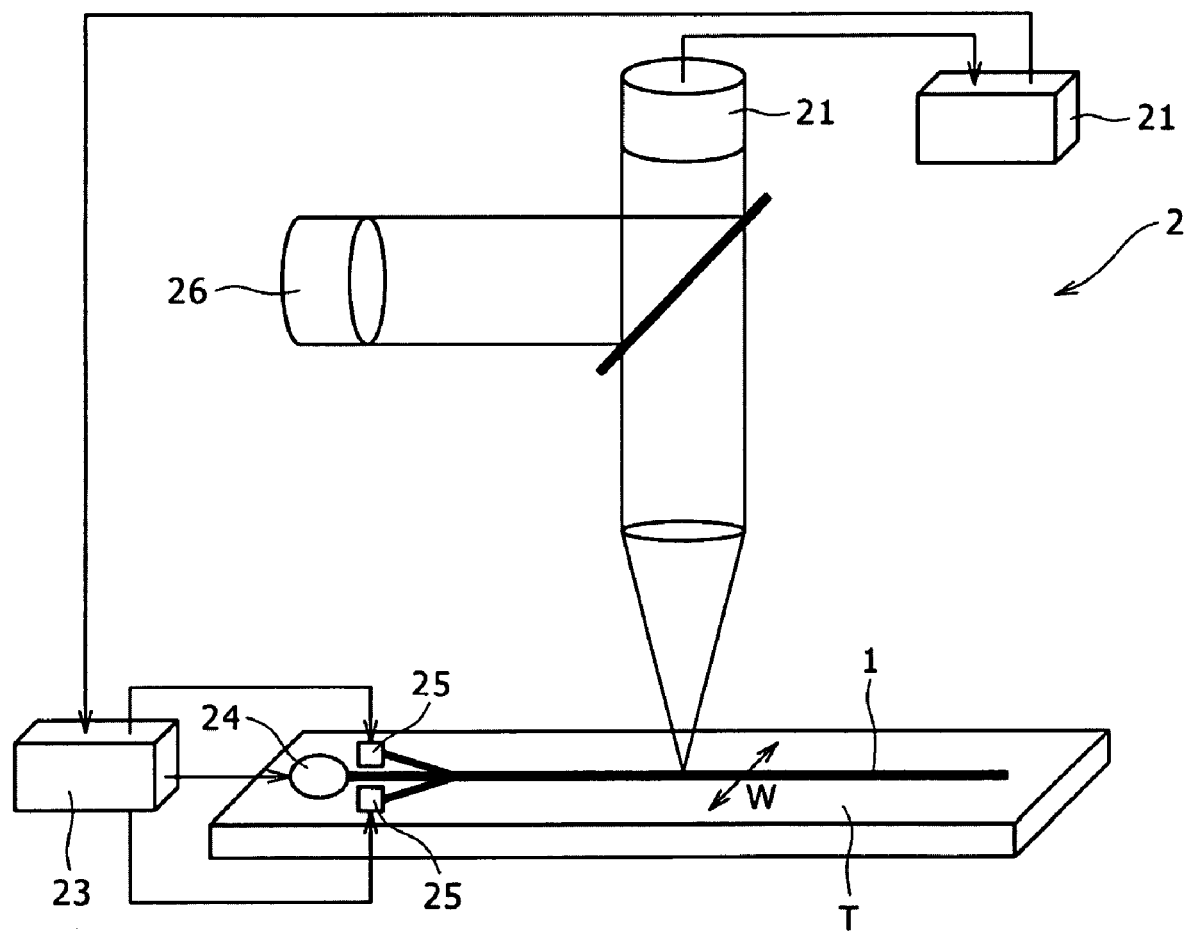
FIG. 16 is a perspective schematic illustration of the concept of a laminar flow control system according to one embodiment of the present invention.

FIG. 16 is a perspective illustration of the concept of a laminar flow control system 2 according to one embodiment of the present invention. The laminar flow control system 2 according to one embodiment of the present invention generally includes at least an optical information detecting section 21, a laminar flow width calculating section 22, and a liquid feed quantity adjusting section 23. Now, the individual sections and the like will be described in detail below.

The form of a channel 1 in which laminar flow widths can be controlled by the laminar flow control system 2 according to one embodiment of the present invention is not particularly limited, and can be designed freely, insofar as laminar flows can be formed in the channel 1. For example, a two-dimensional or three-dimensional channel 1 formed on a substrate formed from a plastic, glass or the like as shown in FIG. 16 can be used to carry out the laminar flow width detecting method according to one embodiment of the present invention.

The channel width of the channel 1 also is not particularly limited, and can be designed freely, insofar as laminar flows can be formed in the channel 1. For example, a micro flow cell with a channel width of 1 mm or below can also be used to carry out the laminar flow width detecting method according to one embodiment of the present invention. Particularly, when a micro flow cell with a channel width of about 10 μm to about 1 mm is used, the laminar flow width detecting method according to one embodiment of the present invention can be carried out more favorably.

In addition, in any of such known channels 1 as shown in FIG. 15, other than the channel 1 exemplified in FIG. 16, it is possible to control the laminar flow width(s) by use of the laminar flow control system 2 according to one embodiment of the present invention.

A plurality of laminar flows are formed in the channel 1. The number of laminar flows of which the widths can be controlled by use of the laminar flow control system 2 according to one embodiment of the present invention is not particularly limited, and can be adjusted according to the purpose. For example, for three laminar flows so formed that a laminar flow of a sample flow F1 containing particulates C to be analyzed and separated is sandwiched between fluid media as denoted by symbol F2 in FIG. 3 (hereinafter referred to as "sheath flows F2"), as shown in FIG. 3, the widths of the individual laminar flows can be controlled. Besides, for two laminar flows, or for four or more laminar flows, also, the widths of the individual laminar flows can be controlled by use of the laminar flow control system 2 according to one embodiment of the present invention.

The formation of the laminar flows (sample flow F1, sheath flows F2) may be carried out externally. However, the formation of laminar flows (sample flow F1, sheath flows F2) may be conducted also by providing, for example, a sample flow pump 24 and sheath flow pumps 25 in the laminar flow control system 2 according to one embodiment of the present invention.

In order to control the widths of laminar flows by use of the laminar flow control system 2 according to one embodiment of the present invention, a reference substance has to be contained in at least one laminar flow selected from among the sample flow F1 and the sheath flows F2. The laminar flow(s) in which the reference substance is to be contained is not particularly limited, and can be appropriately adjusted according to the laminar flow(s) of which the width(s) is to be detected.

The method for containing the reference substance into the sample flow F1 or the sheath flow(s) F2 is also not particularly limited, and can be freely selected from among various methods. For example, a method may be used in which a plurality of laminar flows (sample flow F1, sheath flows F2) are formed in the channel 1, and thereafter the reference substance is contained into the objective laminar flow(s). Also, a method may be used in which a plurality of laminar flows (sample flow F1, sheath flows F2) are formed in the channel 1 by use of fluid medium or media or the like in which the reference substance is preliminarily contained.

The reference substance is not particularly limited, insofar as it permits detection of optical information by an optical information detecting section 21 which will be described later. Examples of the reference substance which can be used include fluorescent substances such as fluorescent coloring matters, etc., and microbeads, etc., among which the fluorescent coloring matters are more preferred in view of the size thereof. The kind of the fluorescent coloring matter to be used can be selected freely. Examples of the fluorescent coloring matter to be used include Cascade Blue, Fluorescein isothiocyanate (FITC), Phycoerythrin (PE), Phycoerythrin-Cy5 (PE-Cy5), Phycoerythrin-Cy7 (PE-Cy7), Texas Red, Allophycocyanin (APC), and Allophycocyanin-Cy7 (APC-Cy7).

In the optical information detecting section 21, optical information from the reference substance contained in the laminar flow(s) (sample flow F1, sheath flows F2) is detected at a predetermined position of the channel 1. Specifically, a laminar flow or flows (sample flow F1, sheath flows F2) containing the reference substance are formed in the channel 1, then a predetermined portion of the channel 1 is irradiated with light by use of a light source 26, as for example shown in FIG. 16, and fluorescence or scattered light generated from the reference substance upon the irradiation with light is detected by a photo-detector or the like in the optical information detecting section 21.

The kind of light irradiation is not particularly limited. However, light which is constant in direction, wavelength and intensity is used desirably, in order for the fluorescence or scattered light to be securely generated from the reference substance and the particulates C. Examples of the light which can be used favorably include laser light and light from an LED (Light Emission Diode).

In the optical information detecting section 21, the light irradiation method is not particularly limited, insofar as the method permits detection of optical information from the reference substance and the particulates C. For instance, the optical information may be detected while scanning an irradiation spot in the channel width direction as indicated by symbol W in FIG. 16.

In the laminar flow width calculating section 22, the widths of the laminar flows (sample flow F1, sheath flows F2) are calculated, based on the optical information detected by the optical information detecting section 21. Specific examples of the calculating method are the same as those in the laminar flow width calculating step (2) in the laminar flow width detecting method described above.

The liquid feed quantity adjusting section 23 adjust the liquid feed quantity (quantities) of the laminar flow(s), based on the laminar flow widths calculated by the laminar flow width calculating section 22. A specific method for this adjustment is the same as that in the liquid feed quantity adjusting step (3) in the laminar flow width control method described above. For example, a method may be used in which the laminar flow width information calculated by the laminar flow width calculating section 22 is transmitted to the liquid feed quantity adjusting section 23, and the sample flow pump 24 and the sheath flow pumps 25 are adjusted based on the laminar flow width information, whereby the liquid feed quantities of the individual laminar flows (sample flow F1, sheath flows F2) can be adjusted.

Then, the liquid feed quantities of the laminar flows (sample flow F1, sheath flows F2) are adjusted at the liquid feed quantity adjusting section 23, whereby the widths of the laminar flows (sample flow F1, sheath flows F2) can be controlled.

Since the widths of the laminar flows (sample flow F1, sheath flows F2) can thus be controlled by the laminar flow control system according to one embodiment of the present invention, control of the width of the sample flow F1 according to the particle diameter of the sample such as the particulates C makes it possible to cause the particulates C to flow in the channel 1 in the state of being orderly arrayed in a row. Therefore, it is possible to enhance the accuracy in analysis and/or separation of the particulates C.

In addition, the widths of the laminar flows (sample flow F1, sheath flows F2) can be controlled according to the light receiving position or size of the light irradiation spot, which also makes it possible to enhance the accuracy in analysis and/or separation of the particulates C, in the same manner as above.

Furthermore, when the reference substance is contained in the sheath flow(s) F2 other than the sample flow F1 containing the particulates C, information from the reference substance other than the particulates C can also be simultaneously detected during the analysis or separation. Therefore, control of optimal optical conditions and electrical conditions or the like for the analysis and separation or the like can be easily carried out even during the analysis or separation. Specifically, the optical conditions include the shape of the irradiation spot, light irradiation intensity, pulse width, the duty ratio of pulses, focal position, etc., whereas the electrical conditions include the amplification factor of the photo-detector, the amplification factor of the light irradiation unit, etc. This realizes shortening of the measurement time and enhancement of the accuracy in analysis or separation or the like.

In addition, when the reference substance is contained in the sheath flows F2, the influence of the surface tension on the wall surface 11 of the channel 1 can be reduced, and the particulates C can be made to flow in the state of being orderly arrayed in a row, whereby the accuracy in analysis and/or separation of the particulates C can be enhanced.

<Flow Cytometer>

Figure 17:
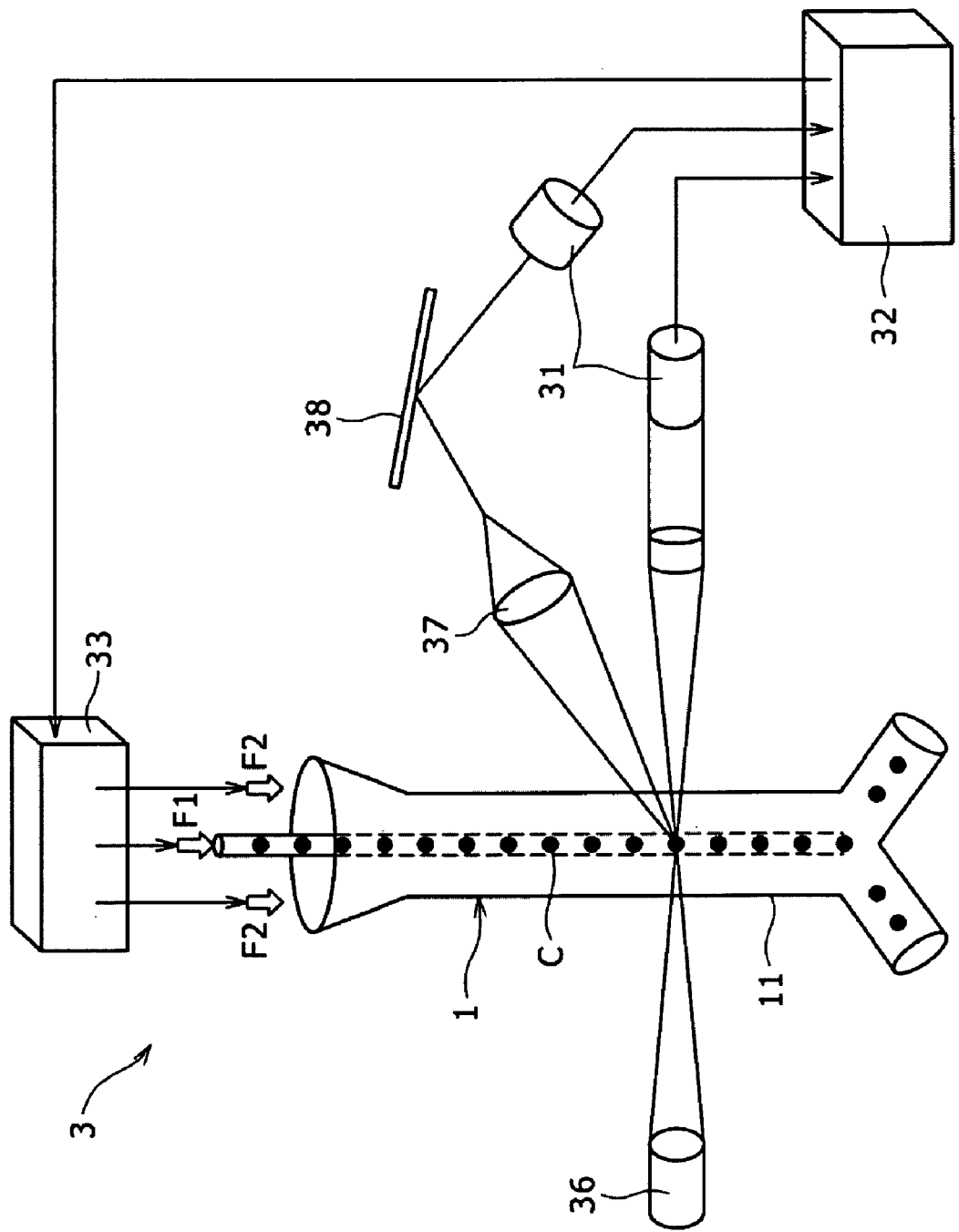
FIG. 17 is a perspective schematic illustration of the concept of a flow cytometer according to one embodiment of the present invention.
Figure 18:
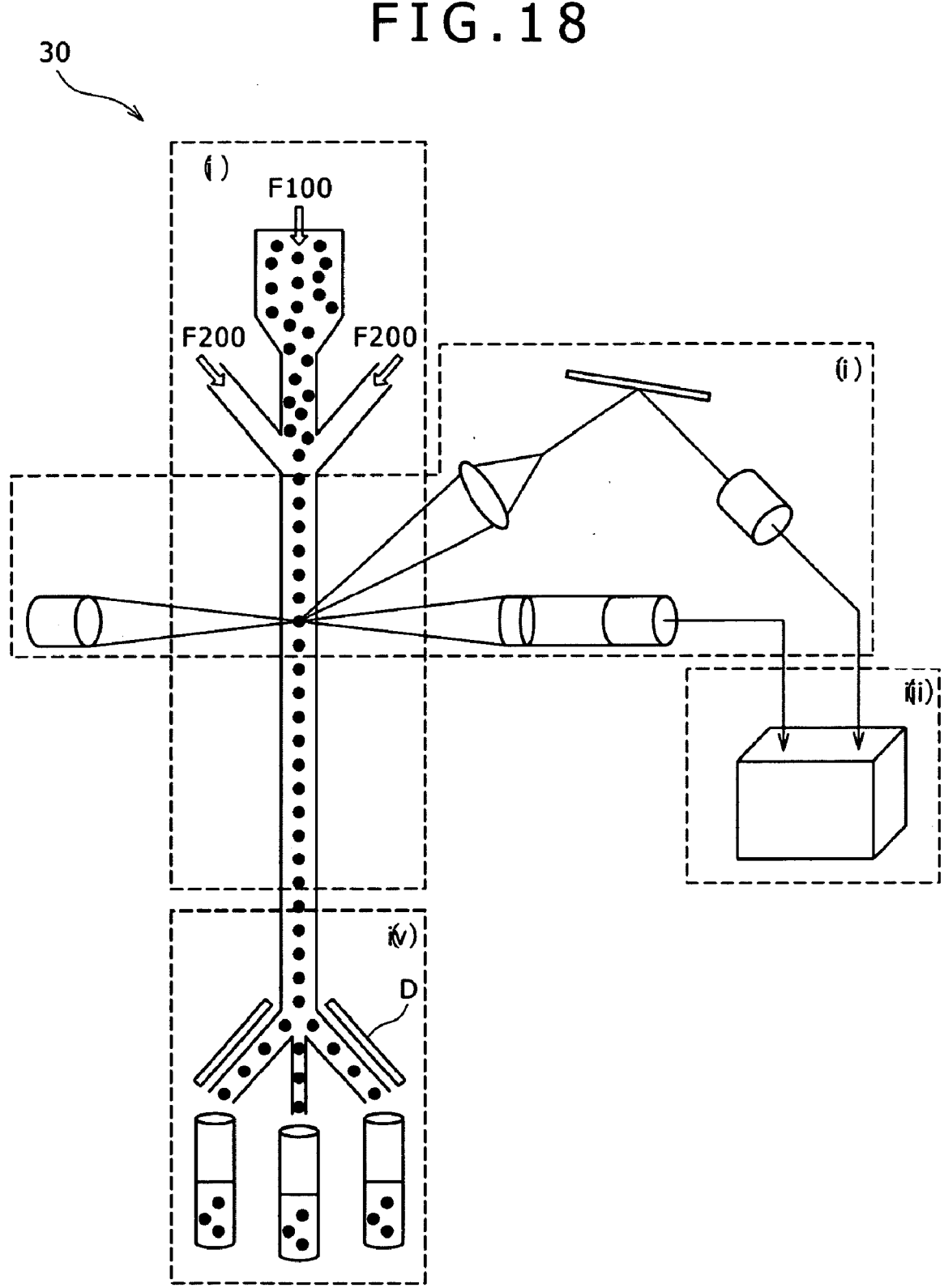
FIG. 18 is a schematic illustration of the concept of a flow cytometer according to the related art.

FIG. 17 is a perspective schematic illustration of the concept of a flow cytometer 3 according to one embodiment of the present invention. The flow cytometer 3 according to one embodiment of the invention generally includes at least an optical information detecting section 31, a laminar flow width calculating section 32, and a liquid feed quantity adjusting section 33. The individual sections will now be described in detail below.

The form of a channel 1 in the flow cytometer 3 according to one embodiment of the present invention is not particularly limited to the channel 1 shown in FIG. 17, and can be designed freely, insofar as laminar flows can be formed in the channel 1. For example, a two-dimensional or three-dimensional channel 1 can be formed on a substrate formed from a plastic, glass or the like.

The channel width of the channel 1 is also not particularly limited, and can be designed freely, insofar as the laminar flows can be formed in the channel 1. For example, a micro flow cell with a channel width of 1 mm or below can be used for the flow cytometer according to one embodiment of the present invention. Particularly, a micro flow cell with a channel width of about 10 μm to about 1 mm is more preferable.

A plurality of laminar flows are formed in the channel 1. The flow cytometer 3 according to one embodiment of the present invention is capable of controlling the widths of laminar flows, irrespectively of the number of the laminar flows. Therefore, the number of the laminar flows is not particularly limited, and can be adjusted according to the purpose. For example, as shown in FIG. 17, in regard of three laminar flows so formed that the laminar flow of a sample flow F1 containing a sample C to be analyzed and separated is sandwiched between fluid media (hereinafter referred to as "sheath flows F2") as denoted by symbols F2 in FIG. 17, the respective laminar flow widths can be controlled. Moreover, also where only two laminar layers are present or where four or more laminar layers are present, the respective laminar flow widths can be controlled by use of the flow cytometer 3 according to one embodiment of the present invention.

The formation of the laminar flows (sample flow F1, sheath flows F2) may be conducted externally. Alternatively, though not shown in the drawings, a sample flow pump and sheath flow pumps may be provided in the flow cytometer 3 according to one embodiment of the present invention, to thereby form the laminar flows (sample flow F1, sheath flows F2).

In order to control the laminar flow widths by use of the flow cytometer 3 according to one embodiment of the present invention, it is needed to contain a reference substance in at least one laminar flow selected from among the sample flow F1 and the sheath flows F2. The laminar flow(s) in which to contain the reference substance is not particularly limited, and can be appropriately adjusted according to the laminar flow(s) of which the width(s) is desired to be detected.

The method by which the reference substance is contained into the sample flow F1 or the sheath flow(s) F2 is not particularly limited, and can be designed freely. For example, a method may be used in which a plurality of laminar flows (sample flow F1, sheath flows F2) are formed in the channel 1, and thereafter the reference substance is put into the objective laminar flow(s). Alternatively, a method may be used in which a plurality of laminar flows (sample flow F1, sheath flows F2) are formed in the channel 1 by use of a fluid medium or media or the like in which the reference substance is preliminarily contained.

The reference substance is not particularly limited, insofar as it permits detection of optical information by an optical information detecting section 21 which will be described later. Examples of the reference substance which can be used include fluorescent substances such as fluorescent coloring matters, etc., and microbeads, etc., among which the fluorescent coloring matters are more preferred in view of the size thereof. The kind of the fluorescent coloring matter to be used can be selected freely. Examples of the fluorescent coloring matter to be used include Cascade Blue, Fluorescein isothiocyanate (FITC), Phycoerythrin (PE), Phycoerythrin-Cy5 (PE-Cy5), Phycoerythrin-Cy7 (PE-Cy7), Texas Red, Allophycocyanin (APC), and Allophycocyanin-Cy7 (APC-Cy7).

In the optical information detecting section 31, optical information from the reference substance contained in the laminar flow(s) (sample flow F1, sheath flows F2) is detected at a predetermined position of the channel 1. Specifically, a laminar flow or flows (sample flow F1, sheath flows F2) containing the reference substance are formed in the channel 1, then a predetermined portion of the channel 1 is irradiated with light by use of a light source 36, as for example shown in FIG. 17, and fluorescence or scattered light generated from the reference substance upon the irradiation with light is detected by a photo-detector or the like in the optical information detecting section 31.

The method of light detection is not particularly limited. Examples of the method which can be used include a method in which the fluorescence or scattered light is condensed by a condenser lens 37 or the like, and is portioned out by a dichroic mirror 38 or the like, to be detected.

The kind of light irradiation is not particularly limited. However, light which is constant in direction, wavelength and intensity is used desirably, in order for the fluorescence or scattered light to be securely generated from the reference substance and the particulates C. Examples of the light which can be used favorably include laser light and light from an LED (Light Emission Diode).

In the laminar flow width calculating section 32, the widths of the laminar flows (sample flow F1, sheath flows F2) are calculated, based on the optical information detected by the optical information detecting section 31. Specific examples of the calculating method are the same as those in the laminar flow width calculating step (2) in the laminar flow width detecting method described above.

The liquid feed quantity adjusting section 33 adjusts the liquid feed quantity (quantities) of the laminar flow(s), based on the laminar flow widths calculated by the laminar flow width calculating section 32. A specific method for this adjustment is the same as that in the liquid feed quantity adjusting step (3) in the laminar flow width control method described above. For example, a method may be used in which the laminar flow width information calculated by the laminar flow width calculating section 32 is transmitted to the liquid feed quantity adjusting section 33, and the liquid feed quantities of the individual laminar flows (sample flow F1, sheath flows F2) can be adjusted, based on the laminar flow width information.

Then, the liquid feed quantities of the laminar flows (sample flow F1, sheath flows F2) are adjusted by the liquid feed quantity adjusting section 33, whereby the widths of the laminar flows (sample flow F1, sheath flows F2) are controlled.

As above-mentioned, in the flow cytometer 3 according to one embodiment of the present invention, the widths of the laminar flows (sample flow F1, sheath flows F2) can be controlled; therefore, control of the width of the sample flow F1 according to the particle diameter of the sample such as the particulates C makes it possible to cause the particulates C to flow in the channel 1 in the state of being orderly arrayed in a row. Accordingly, the accuracy in analysis and/or separation of the particulates C can be enhanced.

Besides, the widths of the laminar flows (sample flow F1, sheath flows F2) can be controlled according to the light receiving position or size of the light irradiation spot, which also makes it possible to enhance the accuracy in analysis or separation of the particulates C, in the same manner as above.

Furthermore, when the reference substance is contained in the sheath flow(s) F2 other than the sample flow F1 containing the particulates C, information from the reference substance other than the particulates C can also be simultaneously detected during the analysis or separation. Therefore, control of optimal optical conditions and electrical conditions or the like for the analysis and separation or the like can be easily carried out even during the analysis or separation. Specifically, the optical conditions include the shape of the irradiation spot, light irradiation intensity, pulse width, the duty ratio of pulses, focal position, etc., whereas the electrical conditions include the amplification factor of the photo-detector, the amplification factor of the light irradiation unit, etc. This realizes shortening of the measurement time and enhancement of the accuracy in analysis or separation or the like.

In addition, with the reference substance contained in the sheath flows F2, the influence of the surface tension on the wall surface 11 of the channel 1 can be reduced, and the particulates C can be made to flow in the state of being orderly arrayed in a row, whereby the accuracy in analysis and/or separation of the particulates C can be enhanced.

It should be understood by those skilled in the art that various modifications, combinations, sub-combinations and alterations may occur depending on design requirements and other factors insofar as they are within the scope of the appended claims or the equivalents thereof.

What is claimed is:

1. A laminar flow width detecting method comprising performing at least the steps of:
    detecting widths of a plurality of laminar flows formed in a channel;
    detecting optical information generated from a reference substance contained in at least one of the plurality of laminar flows;
    calculating the widths of more than two laminar flows, based on the optical information detected in the optical information detecting step;
    wherein the optical information generated from the reference substance is generated at a predetermined position of the channel in which the laminar flows containing the reference substance are formed in the channel, a predetermined portion of the channel is irradiated with light, and fluorescence or scattered light generated from the reference substance upon the irradiation with light is detected by a photo-detector.

2. The laminar flow width detecting method as set forth in claim 1, for detecting the widths of a sample flow and a sheath flow surrounding the sample flow which are formed in a channel in a flow cytometer,
    wherein the reference substance is contained in the sheath flow.

3. The laminar flow width detecting method as set forth in claim 1, wherein the reference substance is a fluorescent substance.

4. A laminar flow width control method comprising performing at least the steps of:
    detecting widths of a plurality of laminar flows formed in a channel;
    detecting optical information generated from a reference substance contained in at least one of the plurality of laminar flows;

calculating the widths of more than two laminar flows, based on the optical information detected in the optical information detecting step;

adjusting the liquid feed quantity of the plurality of laminar flows, based on the widths of the plurality of laminar flows calculated in the laminar flow width calculating step;

wherein the optical information generated from the reference substance is generated at a predetermined position of the channel in which the laminar flows containing the reference substance are formed in the channel, a predetermined portion of the channel is irradiated with light, and fluorescence or scattered light generated from the reference substance upon the irradiation with light is detected by a photo-detector.

5. The laminar flow width control method as set forth in claim 4, for controlling the widths of a sample flow and a sheath flow surrounding the sample flow which are formed in a channel in a cytometer, wherein the reference substance is contained in the sheath flow.

6. The laminar flow width control method as set forth in claim 5, wherein in the liquid feed quantity adjusting step the liquid feed quantities of the sample flow and the sheath flow are adjusted according to the particle diameter of the sample.

7. The laminar flow width control method as set forth in claim 4, wherein the reference substance is a fluorescent substance.

8. A laminar flow control system comprising at least:

width detecting means for detecting widths of a plurality of laminar flows formed in a channel;

optical information detecting means for generating optical information from a reference substance contained in at least one of the plurality of laminar flows;

laminar flow width calculating means for calculating the widths of more than two laminar flows, based on the optical information detected by the optical information detecting means;

liquid feed quantity adjusting means for adjusting the liquid feed quantity of the plurality of laminar flows, based on the widths of the plurality of laminar flows calculated by the laminar flow width calculating means;

wherein the optical information generated from the reference substance is generated at a predetermined position of the channel in which the laminar flows containing the reference substance are formed in the channel, a predetermined portion of the channel is irradiated with light, and fluorescence or scattered light generated from the reference substance upon the irradiation with light is detected by a photo-detector.

9. A laminar flow control system comprising at least:

a width detecting section configured to detect widths of a plurality of laminar flows formed in a channel;

an optical information detecting section configured to generate optical information from a reference substance contained in at least one of the plurality of laminar flows;

a laminar flow width calculating section configured to calculate the widths of more than two laminar flows, based on the optical information detected by the optical information detecting section;

a liquid feed quantity adjusting section configured to adjust the liquid feed quantity of the plurality of laminar flows, based on the widths of the plurality of laminar flows calculated by the laminar flow width calculating section;

wherein the optical information generated from the reference substance is generated at a predetermined position of the channel in which the laminar flows containing the reference substance are formed in the channel, a predetermined portion of the channel is irradiated with light, and fluorescence or scattered light generated from the reference substance upon the irradiation with light is detected by a photo-detector.

* * * * *